United States Patent [19]

Armstrong et al.

[11] Patent Number: 4,906,577
[45] Date of Patent: Mar. 6, 1990

[54] CELL CULTURE BIOREACTOR

[75] Inventors: David W. Armstrong, Ottawa; L. Perry Fleming, Kanata; Deborah G. Grenzowski, Nepean, all of Canada

[73] Assignee: Canadian Patents and Development Ltd., Ottawa, Canada

[21] Appl. No.: 257,003

[22] Filed: Oct. 13, 1988

[30] Foreign Application Priority Data

Jul. 19, 1988 [CA] Canada ................................. 573901

[51] Int. Cl.[4] .............................................. C12M 1/04
[52] U.S. Cl. ..................... 435/313; 435/315; 435/316; 435/286; 435/287
[58] Field of Search ............... 435/313, 315, 316, 311, 435/286, 285, 287; 422/231, 224

[56] References Cited

U.S. PATENT DOCUMENTS

| | | | |
|---|---|---|---|
| 2,244,902 | 6/1941 | Stich | 435/316 X |
| 4,668,632 | 5/1987 | Young et al. | 435/313 X |
| 4,725,548 | 2/1988 | Karrer | 435/313 X |
| 4,746,615 | 5/1988 | Buchholz et al. | 435/313 |
| 4,764,471 | 8/1988 | Ripka | 435/313 X |
| 4,774,187 | 9/1988 | Lehmann | 435/313 |

FOREIGN PATENT DOCUMENTS 414298 2/1974 U.S.S.R. ................................ 435/316

*Primary Examiner*—Larry Jones
*Attorney, Agent, or Firm*—Juliusz Szereszewski

[57] ABSTRACT

There is disclosed a cell culture apparatus particularly suitable for the culture of viable, shear sensitive cells, either grown in suspension or attached to a substrate such as microcarrier beads. The apparatus comprises a cell culture compartment and a compensation chamber disposed thereabove and serving to maintain sterile conditions for the cell culture compartment operating in a zero-headspace mode. The cell culture compartment comprises a gas exchange tube connected to an outside source of gas and defining a downflow zone and a central upflow zone in the cell culture compartment. An Archimedean screw-type auger is installed coaxially in the cell culture compartment to provide a circulating flow of liquid therein. The turbulence of the flow is reduced by the provision of an upper and lower flow guide surface. The gas exchange tube is adapted to exchange gas from outside with the liquid inside the cell culture compartment both on its outer and on its inner surface thereby enhancing the efficiency of gas exchange.

15 Claims, 3 Drawing Sheets

CELL CULTURE BIOREACTOR

BACKGROUND AND PRIOR ART

This invention relates to an apparatus for the culture of cells. The cells to be cultured in this invention are viable, growing or non-growing, prokaryotic and eukaryotic cells such as bacteria, yeast, plant, animal and human cells. These cells may be derived in any manner, that is, isolated from nature, mutated, in the naturally-occurring form, genetically engineered or modified, transformed or non-transformed, hybrids formed by fusion between portions of cells or whole cells of the same or different species. These cells may be attached to the substrate, grown in suspension, or in suspension attached to or within another substrate, such as microcarrier beads or immobilized in some other manner. The cultures may consist of a single cell line or a plurality of cell lines of the same or different species.

Cell lines which produce such proteins as blood factors, interferons, growth hormones and lymphokines are very sensitive to chemical and mechanical stresses (particularly shear forces). Hence their propagation in conventional bioreactors developed for the cultivation of microorganisms with a rigid cell wall is difficult. Many existing bioreactors for animal cell culture have been designed on the principles originally developed for microbial culture, herein referred to as modified microbiol fermentor (MMF) devices (J. Van Brunt, Biotechnology 5: 1134-1138, 1987). These fermentors are aerated by gas overlay and/or sparged air through an open pipe or an open pipe or perforated ring at the bottom of the compartment. Agitation is accomplished by either blade impellers, sail impellers or floating stainless steel mesh stirrers to increase oxygen transfer from gas overlay. These fermentors can also include high-speed rotating stainless steel mesh cylinders for perfusion. These latter means of agitation generally impart turbulent flow characteristics. The bases of the vessels range from flat to slightly rounded to hemispherical. Some of the adaptations of hardware (e.g. hemispherical base) have been successful although these particular animal cell culture devices are limited to only certain types of cells. The major drawback of the MMF is the fluid and mechanical shearing associated with the sparged air and agitation impellers used for gas transfer and minimizing zones of excess nutrients or titrants (pH control).

Other devices utilizing indirect gas transfer, such as gas-permeable membranes or 'caged' aeration systems have been developed. The design features including the use of silicone tubing windings (see: U.S. Pat. No. 4,649,114) and stainless steel mesh cylinders (see: U.S. Pat. No. 4,727,040) would be technically difficult or economically prohibitive on scale-up units. The manufacturing costs for large scale fine-mesh components of the gas exchange system could be very high. As well, problems related to shear forces generated due to rotation of the cylinder, which minimizes biofouling, are detrimental to cell integrity (A. J. Brennan, New Brunswick Tech. Bull. D-01406-02-87, 1987). Agitation is provided by a blade impeller or pressure-differential. The bases of the vessels range from flat to slightly rounded to hemispherical.

Classical airlift systems with a concentrically-placed, or occasionally non-concentric configuration, draft tube or component with similar function within the vessel have been implemented for animal cell culture (J. Van Brunt, 1987, op.cit.). These systems tend to induce strong fluid shear forces which can be extremely detrimental to growth and/or productivity. Normally these systems drive air in at the base of the vessel to create a density difference in the liquid. The rising liquid not only imparts oxygen for growth and metabolism but also lifts the cells and mixes the liquid. However, as the bubbles rise they coalesce into larger bubbles and upon contacting the surface of the liquid the bursting bubbles create extreme shear stress on the cells (bubble shear) leading to metabolic stress or even cell destruction.

There has recently been a report of a bubble-free aeration system (R. Wagner and J. Lehmann, TIB-TECH 6(5), 101-104, 1988). This system comprises a hydrophobic membrane made of polypropylene that is formed as a porous hollow fiber. Bubble-free aeration is achieved if the internal gas pressure does not exceed the pressure at which the bubbles will form. The hydrophobic membrane is looped around a carrier that is slowly moved through the culture to produce a membrane stirrer. This system would be difficult to scale-up. Cells and microcarriers would probably become trapped on the membrane. Dead zones would be present within the system and the hydrodynamics would be unpredictable.

Another alternative technology for animal cell culture is fluidized bed reactors. The cells are immobilized by hydrogel encapsulation or entrapment and air is sparged at the base of the vessel. The vessels have a large height to diameter ratio and have cylindrical or conical bases. The immobilization requirements limit the system's versatility and would present difficulties in scale-up.

Cells have also been immobilized on an inorganic cylindrical (ceramic) support matrix with micro-channels for direct infusion of oxygenated medium. Such support matrices cannot be reused. Scale-up of such a system would be expensive with labor intensive operation and maintenance.

U.S. Pat. No. 4,661,458 teaches a system wherein the cells are provided on an organic tubular or laminate membrane cell support. Such a system would provide for the formation of non-homogeneous microenvironments. The growth of cells on such a support can impede mass transfer of nutrients and gases.

In summary, problems with currently available cell culture technologies include: fluid and mechanical shear; supply of oxygen; measurement and control of the system; formation of gradients (pH, dissolved oxygen, temperature and nutrients); removal of products and wastes, gaseous or non-gaseous in nature; versatility and potential for scale-up.

The ideal animal cell bioreactor design requires:
(a) An agitation system which provides gentle and predictable flow patterns and optimized mass transfer. Mixing must also be sufficient to minimize gradients within the vessel while avoiding mechanical shear.
(b) The use of indirect gas transfer through a gas-permeable membrane because of the fluid and mechanical shear associated with the aeration systems of existing technologies.
(c) That there be ideally effective real-time measurement and control of growth and production parameters.
(d) A means for product and waste product removal which is not affected over long runs by biofouling of the device.

(e) That the system be versatile; ideally it should be applicable to shear-resistant and shear-sensitive cell lines in microcarrier and suspension culture. The bioreactor should be able to operate in the batch, fed-batch, repeated fed-batch, perfusion and continuous modes.

(f) That the system be scaleable.

A scaleable bioreactor incorporating the above-mentioned features having capability to be operated in various modes as outlined would be desirable.

SUMMARY OF THE INVENTION

According to the invention, there is provided a cell culture apparatus comprising:
(a) a cell culture compartment having a side surface and two opposite flow-directing surfaces defining together a low-turbulence internal compartment surface,
(b) a compensation chamber disposed above said compartment in fluid communication therewith,
(c) a gas exchange tube disposed within said compartment and having opposite open ends facing each one of the flow directing surfaces, the gas exchange tube having an inner surface and an outer surface, both surfaces being provided with gas exchange means for supplying and removing gases to and from the culture medium,
(d) gas conduit means communicating with the gas exchange means from outside the compartment; and
(e) liquid-lifting means disposed within said compartment substantially coaxially with the gas exchange tube.

Preferably, mechanical liquid-lifting means providing a relatively gentle, turbulence-free liquid displacement are used, for example an Archimedean screw. The liquid lifting means are preferably equipped with scooping means to prevent the formation of a "dead zone" at the bottom of the compartment.

BRIEF DESCRIPTION OF THE DRAWINGS

In the drawing which illustrates an embodiment of the invention

DETAILED DESCRIPTION OF THE INVENTION

Figure 1:
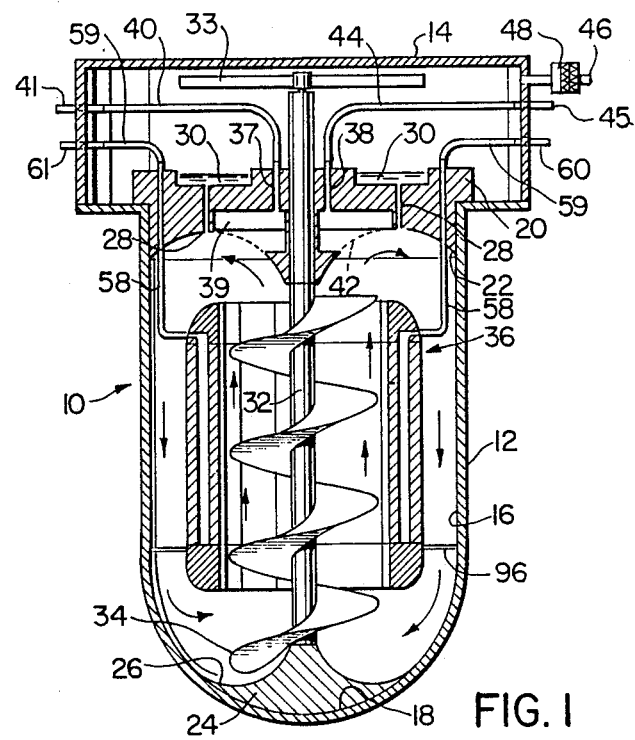
FIG. 1 is a vertical sectional view of a cell culture bioreactor filled with a culture medium.

Referring now to FIG. 1, there is illustrated a cell culture apparatus 10 which can be used for the suspension cultivation of mammalian and other animal cells or shear-sensitive plant or microbial cells. The apparatus 10 consists of a cell culture compartment 12 and a cylindrical compensation chamber 14 which is disposed above the compartment 12 and has a larger diameter than the compartment. Both the chamber 14 and the compartment 12 are made of clear glass but may also be made of non-toxic rigid plastic materials or of biocompatible metals such as, for example, stainless steel. The compartment 12 has a cylindrical wall 16 and a hemispherical bottom 18. The shelf formed between the compartment 12 and the chamber 14 serves to support a removable bulkhead 20 which has on its lower side an annular arcuate recess 22 which serves as a top flow guide. An attachment means (not illustrated) is provided to fasten the bulkhead 20 releasably to the compartment 12 so as to eliminate its rotation or lifting during operation. At the bottom 18 of the compartment there is provided a flow directing element 24 having an annular arcuate recess 26 which serves as a bottom flow guide. The bottom flow guide could be a non-porous insert or it could be an integral part of the compartment wall.

In large-scale bioreactors it is possible to install a piston-type harvesting valve joining the compartment 12 through the flow-directing element 24. The valve in its closed position would conform to the surface of the element 24 and in its open position provides a drain for aseptic draining of fluids.

The apparatus is adapted to operate preferably in a zero-headspace mode, wherein the cell culture compartment is filled entirely with a cell culture medium. Even when the apparatus is operated in a bubble-free manner, some outgassing of the medium could occur along with coalescence of metabolic $CO_2$, especially over extended periods of time. The compensation chamber 14 is provided to accommodate changes in volume of liquid in the cell culture compartment and changes in pressure therein. To that effect, the bulkhead 20 has a number of channels 28 which communicate with the compartment 12 at the uppermost area thereof. This facilitates the outgassing of the compartment 12. On the upper side, the bulkhead 20 has an overflow well 30 which acts as a reservoir for excess liquid from the compartment 12 to ensure zero-headspace.

The provision of the compensation chamber also allows for maintaining the sterility of the cell culture when the apparatus is operated in a zero-headspace mode.

Positioned vertically within the compartment 12 is a rotatable auger 32 with a shaft which is mounted on the bottom flow directing element 24 on one end and passes through the bulkhead 20. In the embodiment illustrated, the auger is an Archimedean screw driven by a magnetic drive which is indicated schematically as a magnetic couple 33. The provision of a magnetic drive eliminates the necessity of creating another microbiological seal for the bioreactor. However, other direct mechanical drive means penetrating through appropriate mechanical seals could be used. The preferred pitch angle of the auger is about 22°, however the angle may be varied depending upon the ultimate use of the bioreactor and compartment geometry. The pitch angle may be a constant angle for all flights and as well there may multiple flights. Various angles may also be employed in one or more regions of the auger. Flights with essentially flat surfaces with rounded edges could be used although other configurations incorporating curved (concave) surfaces could be employed to ensure proper fluid flow. It is also conceivable that the auger may be an oblique helicoid rather than a right helicoid as shown.

A plough-like scooping element 34 is incorporated onto the auger 32 on its leading edge. The element 34 has a lower edge which is of a shape corresponding with the shape of the recess 26 and is distanced by ideally about 3 mm from the surface of the recess 26. This results in the element 34 lifting the medium from the lowermost area of the compartment 12 thus eliminating dead zones therein, while shearing and scraping of the cells is avoided. The auger is shown with one plough unit on its leading edge. Multiple plough units may be added if necessary depending on process requirements.

A gas exchange tube 36 is provided within the compartment 12 coaxially therewith. The gas exchange tube, also referred to hereinafter as GET, surrounds the auger 32 over most of its length and defines an upward flow zone inside the tube and a downward flow zone between the tube 36 and the cylindrical wall 16 of the compartment, when the auger 32 is in operation.

The top and bottom flow guides 22 and 26 serve to provide a gentle predictable flow pattern when the cell culture compartment 12 is filled with liquid and the auger 32 is in operation. The configuration of the flow guides 22, 26 is such as to minimize the turbulence and, consequently, reduce the possibility of damage to shear-sensitive cells.

The bioreactor can be used in a continuous mode or batch, fed-batch, repeated fed-batch or perfusion mode. In a batch mode, no products of cell metabolism would be removed from the compartment during the operation. On the contrary, in a perfusion mode, the products of metabolism are constantly removed from the compartment via narrow channels 37, provided in the bulkhead 20 and via associated tubing 40 and 41 connected to a liquid pump, not illustrated. The channels 37, 38 communicate with a perfusion chamber 39 which is separated from the compartment 12 by a porous perfusion element 42. The perfusion element 42 acts as a filtering element for the medium drawn from the cell culture compartment through the channel 37. In the embodiment illustrated in FIG. 1, the perfusion element 42 is a defined porous hydrophilic ring which corresponds in size to the perfusion chamber 39. Alternatively, the whole surface of the top flow guide 22 in contact with the liquid may be of a porous nature. The porosity of the element 42 should be such as to allow the passage of certain metabolites or cell products of interest but prevent the passage of cells. The element 42 can be made of microporous porcelain, sintered stainless steel, plastic, or other such rigid or semirigid microporous biocompatible material. A pore size of from about 0.2 $\mu$m to about 5.0 $\mu$m is suitable for most single cells. In the case of cell aggregates or cells attached to microcarriers, the pore size can be larger but still smaller than the particles to be filtered, e.g. a pore size from about 25 $\mu$m to about 75 $\mu$m in the case of particles of about 100 $\mu$m in diameter or larger. The fluid containing the product(s) of interest would collect within the body of the top flow guide and then be drawn off through the tubing 40 and 41 to the outside of the compartment for appropriate concentration and processing.

The porous insert 42 may be susceptible to plugging or fouling by cells or components thereof during the operation of the bioreactor. To avoid such undesirable occurrence, two measures are introduced. The flow of liquid from the upward flow zone is essentially tangential to the upper flow guide surface 22 thereby acting to remove, at least partly, the fouling matter from the porous insert 42. Further a tubing 44 and 45 is provided to be connected to a channel 38 and to a source of nitrogen or another gas, not illustrated. Brief intermittent bursts of nitrogen through the tubing 44, the associated channel 38 and the element 42 would clear the latter from biofouling while the withdrawal of perfusate through the tubing 40 would continue without perturbation. In order that the bulkhead 20 can be removed from the chamber 14, both tubing 40 and 44 are attached to tubes 41 and 45, respectively, which communicate with the inside and the outside of the chamber 14.

The compensation chamber is provided with a vent 46 associated with a microbiological filter 48. This enables the equalization of pressure in the chamber 14 following the changes of liquid volume in the compartment 12 and gas exchange between the compartment and the chamber 14.

Figure 2:
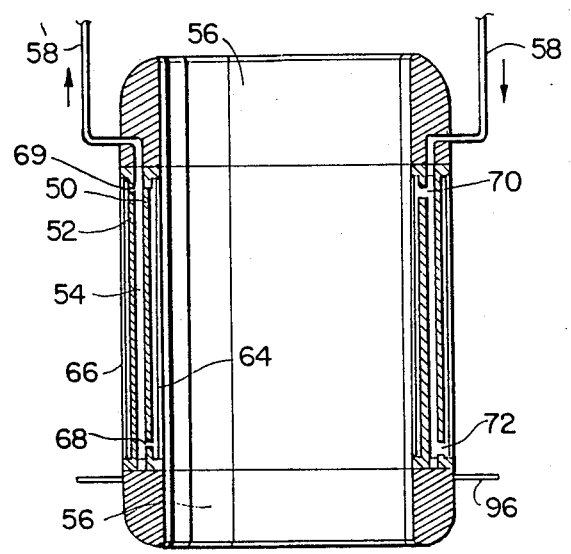
FIG. 2 is a vertical sectional view of one embodiment of the gas exchange tube.
Figure 3:
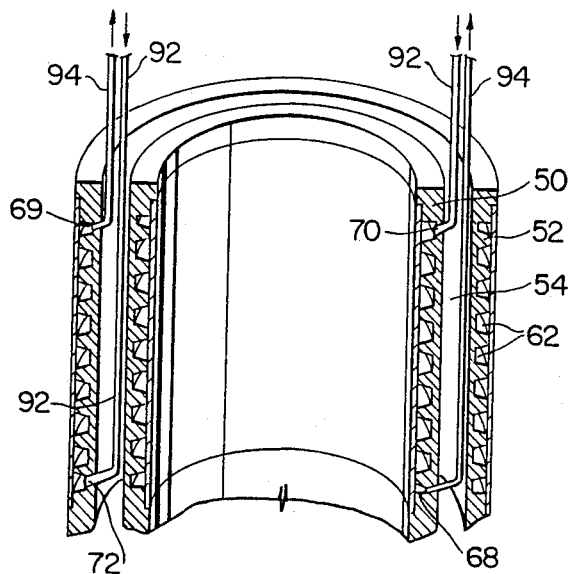
FIG. 3 is a partial sectional view of another embodiment of the gas exchange tube.
Figure 3A:
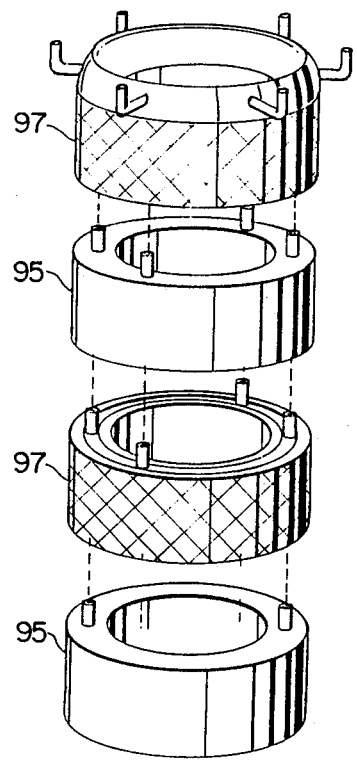
FIG. 3a is an exploded partial view of a modular embodiment of the gas exchange tube.

Several embodiments of the gas exchange tube are illustrated in more detail in FIGS. 2, 3 and 3a. In the embodiment of FIG. 2, the GET consists of an inner wall 50 and an outer wall 52. The walls define a passage 54 therebetween which is closed on both ends by annular covers 56. The upper cover 56 (FIG. 2) has two tubes 58 which are communicated with gas conduits 60 and 61 by tubing 59 (FIG. 1). In this embodiment, one conduit 60 is connected with a source of gases (air, oxygen, nitrogen and $CO_2$) located outside the cell culture compartment, not illustrated in the drawing. The other conduit 61 serves to discharge the gases that enter the gas exchange tube from the cell culture medium.

The interior side of the inner wall 50 and the exterior side of the outer wall 52 are provided with grooves 62 (shown in FIG. 3) which extend in a form of spiral between the upper and the lower end of the walls 50, 52 respectively. The grooves are covered with two cylindrical gas permeable membranes 64, 66 which are bonded to the respective walls 50, 52 making contact with the crests of the grooves. The gas conduits 60 shown in FIG. 1, are connected to the grooves 62 in the inner wall 50 and the outer wall 52 through gas inlet ports 70, 72 respectively. Consequently, gases such as air, oxygen, nitrogen or $CO_2$ are supplied to the grooves 62 through the conduits 60 and inlet ports 70, 72 and then pass through the membranes 64, 66 to the cell culture medium on the upflow side and the downflow side of the GET. The gases enter the liquid medium virtually bubble-free and exchange with the gases evolved from the cultured cells. The gas outlet ports 68 and 69, from the inner wall 50 and outer wall 52 respectively, are of a smaller diameter than the gas inlet ports 70, 72 to allow for a slight back pressure. While in the drawing, the GET is shown to be a right cylinder, it is understood that the GET could be conoid in shape with appropriate modifications to the geometry of the liquid lifting system.

In the embodiment of FIG. 2, gases are supplied to the liquid preferentially in a counter-current manner or otherwise, wherein the gas inlet ports are located at the top of the GET on its upflow side and at the bottom of the GET on its downflow side. Gases that enter the passage 54 through the outlet ports 68 and 69 leave the passage through conduit 61 as illustrated in FIG. 1.

In large bioreactors the passage 54 may be large enough to allow direct connection between the gas conduits 60 and the grooves 62. In this embodiment, shown in FIG. 3, two gas conduits deliver gases to the grooves 62 by tubing 92 in the inner wall 50, and outer wall 52 through gas inlet ports 70 and 72 respectively. As in the embodiment shown in FIG. 2, the gases are supplied to the liquid preferentially in a counter-current manner, wherein the gas inlet ports are located at the top of the GET on its upflow side and at the bottom of the GET on its downflow side. Gases leaving the culture medium do so from the outlet ports 68 and 69, from the inner wall 50 and outer wall 52, respectively, connected to tubing 94. The arrangement of tubings 92 and 94 illustrated in FIG. 3, is schematical only. In practice, the tubings may be connected to their respective ports at points spaced over the periphery of the gas exchange tube as shown in FIG. 3a.

The GET could also be used in a modular manner with solid inserts 95 placed between respective gas exchange membrane sections 97 (FIG. 3a). Such inserts would have the appropriate channels for gas inlet and outlet passing through the insert to connect respective gas exchange tubes. As shown in FIG. 3a, a pair of channels is provided to serve gas supply and discharge for each gas exchange tube. Thus, the individual gas exchange modules could be controlled independently as an increased hydrostatic pressure progressing down the cell culture compartment would be encountered. This would allow for uniform exchange of gases throughout the gas exchange tube. Sensors could be placed at various levels to ascertain the local conditions.

In an alternative design, the GET could be a solid tube with slots cut in its surface. Gas-permeable tubing could be wrapped around the outer surface of this tube with inlet and outlet connections being made through the bulkhead.

The GET is supported in the vertical plane by supports or the gas inlet and outlet tubes which enter the cell culture compartment through the bulkhead 20. Movement of the GET in the horizontal plane is restricted by supports 96 preferably attached to the GET but also possibly attached to the cell culture compartment wall.

Gases supplied to the medium to sustain cell metabolism may be enriched with $CO_2$ which will have the effect of acidifying the liquid in the cell culture compartment, thus lowering its pH. Alternatively, enriching gases with nitrogen will effectively strip $CO_2$ from the liquid thereby raising the pH. This control of pH could be augmented by the use of liquid acid/base titrants.

It is important that all the structural elements within the cell culture compartment are of a shape that does not promote flow turbulence and eliminates sedimentation on the membrane In the embodiments illustrated, such conditions are met by the provision of substantially flat membranes rather than spiral gas-permeable tubing, in addition to the top and bottom flow guiding surfaces.

The control system of the cell culture apparatus of the invention includes level control. As the apparatus is mainly designed to operate in a zero-headspace mode to eliminate foaming and shearing forces generated at the liquid surface, the overflow well 30 of the compensation chamber is adapted to hold the excess liquid at a level above the uppermost area of the cell culture compartment. The level of liquid in the well is controlled by a level sensor means, not illustrated in the drawing The sensor is connected to a controller which regulates a pump so that level fluctuations in the overflow well will result in the pump supplying additional amounts of the medium or removing it.

Figure 4:
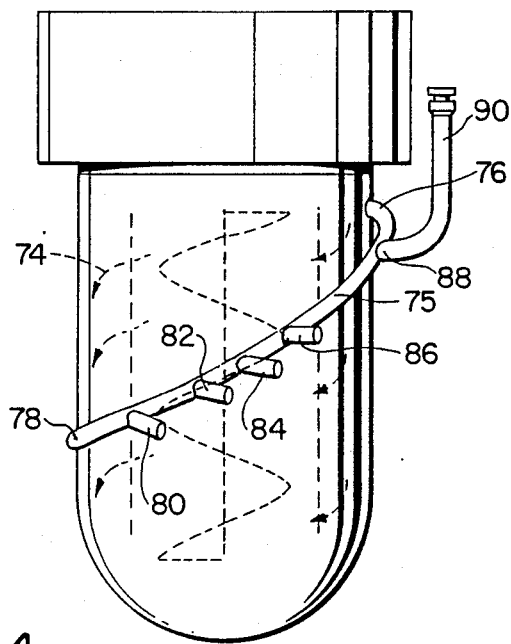
FIG. 4 is a view of the bioreactor with an external control sensor circuit.
Figure 5:
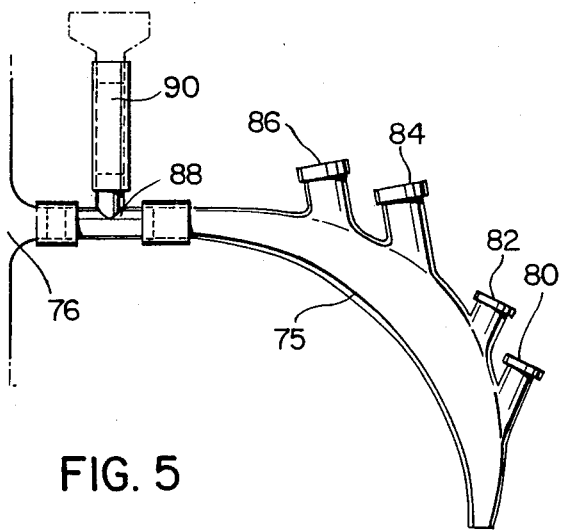
FIG. 5 is a view of the external sensor circuit attached to the top diverticulation port of the bioreactor.

An external control sensor circuit is illustrated in FIGS. 4 and 5. The design of the circuit takes advantage of the liquid flow pattern created within the cell culture compartment by the action of the auger 32. As indicated in FIG. 4 with arrows 74, the liquid in the downflow zone flows at an angle intermediate between the horizontal and vertical axis. Accordingly, the control circuit comprises a tubing 75 which is connected to the compartment at an inlet port 76 and at an outlet port 78 which is situated at a lower level than the inlet port 76, so that the tubing 75 extends at an angle approximately corresponding to the generated angle of liquid flow in the downflow zone of the compartment. This results in the diverticulation of a representative sample of liquid from the upper outermost region of the downflow zone of the compartment, accomplished with or without supplementary means. The angle of the inlet and outlet ports 76, 78 should preferably allow for efficient non-disruptive fluid flow through the control circuit.

The control circuit comprises, by way of example, a number of connections adapted for suitable monitoring equipment. These connections 80, 82, 84, 86 and 88 join the tubing 75 at an acute angle (downwards with the fluid flow through the tubing 75) so as to minimize the flow turbulence. This is illustrated in FIG. 5. The connections 80-86 accommodate a sampling device, a titrating infusion device, a pH probe and a dissolved oxygen probe, although other ports or sensors, as required, can be incorporated. The connection 88 is for a removable filling tube 90. The upper end of the filling tube is at a higher level than the level of the overflow well, thus making it possible to introduce the liquid and/or inoculum to the compartment to fill it completely, while the gases from the compartment would be displaced through channels 28 into the chamber 14 and then discharged through the vent 46 and the filter 48.

The cell culture apparatus of this invention is adaptable for use with all types of animal cells including, for example, mammalian, amphibian, insect, fowl, as well as plant cells. Primary cells taken from embryonic, adult or tumor tissues as well as continuous cell lines can thus be used. These are all well known cell lines which are available to the public for research and other purposes from various depositories.

The cell culture apparatus of this invention also is adaptable to use with any of the well known tissue culture media such as, for example, Basal Medium Eagle's (BME), Eagle's Minimum Essential Medium (MEM), Dulbecco's Modified Eagle Medium, Medium 199, and the like. These conventional culture media contain known essential amino acids, mineral salts, vitamins and carbohydrates. They are also frequently fortified with mammalian sera such as fetal bovine serum.

Various other examples will be apparent to the person skilled in the art after reading the disclosure herein without departing from the spirit and scope of the invention. It is intended that all such further examples be included within the scope of the appended claims. It is also to be understood that the following claims are intended to cover all of the generic and specific features of the invention herein described and all statements of the scope of the invention which , as a matter of language, might be said to fall therebetween.

What is claimed:
1. A cell culture bioreactor comprising:
a cell culture compartment having a side surface and two opposite liquid flow-directing surfaces defining together a low-turbulence internal compartment surface,
a compensation chamber disposed above said compartment in fluid communication therewith,
a gas exchange tube disposed within said cell culture compartment and having opposite open ends facing each one of the flow-directing surfaces, the gas exchange tube having an inner gas permeable sur- face and an outer gas permeable surface, both surfaces being provided with gas exchange means for supplying and removing gases to and from a culture medium in the compartment, a gas conduit means communicating with the gas exchange means from outside the compartment; and liquid-lifting means disposed within said compartment.

2. An apparatus according to claim 1 in which the compensation chamber has an overflow cell at its bottom, the well being in fluid communication with the uppermost area of the cell culture compartment.

3. An apparatus according to claim 2 adapted to be filled with a liquid up to the overflow well and provided with a level sensor and a liquid pump connected to a controller and the sensor for controlling the volume of liquid in the cell culture compartment and the overflow well.

4. An apparatus according to claim 1 wherein at least a part of the upper flow directing surface is defined by a perfusion element which is in fluid communication with a product conduit for removing cell culture products from the cell culture compartment, and with a source of gaseous nitrogen or another gas for defouling the perfusion element.

5. An apparatus according to claim 1 wherein the liquid-lifting means is driven by a mechanical drive means.

6. An apparatus according to claim 5 wherein the mechanical drive means is a magnetic drive means.

7. An apparatus according to claim 1 in which the inner surface and the outer surface of the gas exchange tube define a gas cavity therebetween, the cavity being in fluid communication with the gas conduit means, the inner surface and the outer surface being covered each with a gas permeable membrane and openings being provided in the surfaces to communicate the gas cavity with the respective membranes.

8. An apparatus according to claim 7 wherein the gas permeable membrane is substantially flat.

9. An apparatus according to claim 7 wherein the gas permeable membrane is a tubular membrane.

10. An apparatus according to claim 7 wherein the gas exchange tube is modular with solid inserts placed between respective gas permeable membranes.

11. An apparatus according to claim 1 wherein the liquid-lifting means are adapted to create a spiraling downward flow of liquid outside the gas exchange tube in the compartment, the compartment having an external liquid conduit adapted to connect sensing devices thereto, the conduit being connected to the cell culture compartment at both ends and extending at an angle to the vertical approximately consistent with the direction of the spiral liquid flow when generated outside the gas exchange tube.

12. A cell culture apparatus according to claim 1, comprising a generally cylindrical side surface, an upper flow directing surface and a lower flow directing surface, wherein the liquid-lifting means are mechanical liquid displacement means disposed substantially coaxially with the gas exchange tube.

13. A cell culture apparatus according to claim 12 in which the liquid-lifting means is an Archimedean screw disposed coaxially with, and at least partly within, the gas exchange tube.

14. An apparatus according to claim 12 in which the upper and the lower flow directing surfaces are annular concave surfaces concentric to the gas exchange tube and adapted to enable a low-turbulence flow of liquid, when moved with the liquid-lifting means, between the space outside the gas exchange tube and the space inside the gas exchange tube.

15. A cell culture apparatus according to claim 12 wherein said liquid lifting means are provided with a scoop element extending downwardly in proximity with the lower flow-directing surface and conforming in shape thereto.

* * * * *